United States Patent [19]

Horn et al.

[11] Patent Number: 5,670,660

[45] Date of Patent: Sep. 23, 1997

[54] PROCESS FOR COLLECTING AIRBORNE ANHYDRIDES

[75] Inventors: Ronald H. Horn; Lee W. Barwick, both of West Bend, Wis.

[73] Assignee: Cook Composites and Polymers Co., Kansas City, Mo.

[21] Appl. No.: 349,824

[22] Filed: Dec. 6, 1994

[51] Int. Cl.$^6$ ................................................ C07D 307/36
[52] U.S. Cl. ........................ 549/262; 549/245; 549/231; 549/250; 549/251
[58] Field of Search ........................ 549/245, 262, 549/231, 250, 251

[56] References Cited

U.S. PATENT DOCUMENTS

| | | | |
|---|---|---|---|
| 2,140,140 | 12/1938 | Punnett | 260/343 |
| 3,818,680 | 6/1974 | Marquis | 55/48 |
| 3,850,758 | 11/1974 | Smith et al. | 203/38 |
| 3,891,680 | 6/1975 | Katsumoto et al. | 260/346.8 M |
| 3,965,123 | 6/1976 | Franklin | 260/346.8 M |
| 4,118,403 | 10/1978 | White | 260/346.76 |
| 4,314,946 | 2/1982 | Neri et al. | 260/346.76 |
| 5,069,687 | 12/1991 | Bertola et al. | 55/44 |
| 5,126,463 | 6/1992 | Ramachandran et al. | 549/262 |
| 5,210,223 | 5/1993 | Chen et al. | 549/247 |

Primary Examiner—Samuel Barts
Attorney, Agent, or Firm—Whyte Hirschboeck Dudek S.C.

[57] ABSTRACT

An apparatus and process for the recovery of airborne anhydrides such as anhydride vapor or dust wherein these airborne anhydrides are contacted with hot glycol, such as diethylene glycol, in the liquid phase to first dissolve and then react with the airborne anhydrides yielding a useable by-product, such as half-esters. In the preferred embodiment, first airborne anhydrides are introduced at the top of a venturi where the anhydrides are contacted with diethylene glycol of at least 270° F. The airborne anhydrides dissolve in the glycol and then react with the glycol to form a solution of half-esters and glycol. The venturi enhances the contact between the glycol and the first airborne anhydrides, facilitating the dissolution of the anhydrides in the glycol. Second airborne anhydrides are introduced at the discharge side of the venturi such that the second airborne anhydrides dissolve in unreacted hot glycol and then react to form additional half-esters. The solution of half-esters and unreacted glycol then flow into a collection tank from which the solution is circulated back through the system. Any residual airborne anhydrides remaining after the venturi are directed through a packed column. In the packed column, these airborne anhydrides are again contacted with the glycol solution such that the airborne anhydrides dissolve and react to form half-esters.

19 Claims, 2 Drawing Sheets

PROCESS FOR COLLECTING AIRBORNE ANHYDRIDES

BACKGROUND OF THE INVENTION

1. Field of the Invention

This invention is concerned with an improved environmental control apparatus and process for the collection of anhydride vapor, such as maleic or phthalic anhydride vapor, or anhydride dust, such as trimellitic or succinic anhydride dust, that results from the storage of anhydrides. More particularly, the process utilizes hot liquid glycol, such as diethylene glycol, to absorb and react with these anhydride vapors and/or dust, resulting in a useable half-ester product which does not require further refinement.

2. Prior Art

Anhydrides are useful chemicals in the production of processed materials such as polyesters. More specifically, these anhydrides can be used to form raw material, such as half esters, which can be further processed to produce a final product. For example, half esters can be used to produce thermoset resins, thermosetting polyester resins, thermosetting acrylic vinyl ester polymers, alkyds, etc. Although anhydrides are typically stored in liquid, i.e. maleic or phthalic, or solid, i.e., trimellitic or succinic, form, it is possible that a portion of these anhydrides will become airborne either as a vapor or as a dust while in their storage containers. The problem of airborne anhydride vapor and/or dust becomes even more severe as additional anhydride is loaded into the storage containers because large volumes of these vapors and/or dust are displaced from the anhydride storage containers during loading. Release of these airborne anhydrides into the atmosphere is environmentally undesirable. For example, maleic anhydride vapor is toxic and phthalic anhydride vapor is a membrane irritant. Therefore, there is a need to capture and dispose of anhydride vapor and/or dust in an environmentally safe manner.

In the past, the problem of vaporous anhydride has been addressed in a variety of manners including venting the storage tanks to the atmosphere or directing the vaporous anhydride through a series of cold boxes to condense the vapors. Because of the lack of environmental regulations, alternative disposal methods for maleic and phthalic anhydride vapors have not been vigorously pursued. The same is true for anhydride dust. Yet with increased environmental regulations and a heightened awareness of the hazardous characteristics of these airborne anhydrides, it has become necessary to develop more effective methods for collecting and disposing of airborne anhydrides, whether in vapor form or dust form.

One solution to collect anhydride vapors is to implement the industrial processes used to scrub maleic and phthalic anhydride vapors from gaseous mixtures that are typically present during the production of maleic and phthalic anhydride. These processes have been developed because gaseous and vaporous mixtures containing anhydrides are often produced as by-products in various industrial processes. Given the usefulness of maleic and phthalic anhydrides, it is often economically desirable to capture these vaporous by-product anhydrides and purify the anhydrides for sale. The prior art is replete with methods for separating the anhydride component from gaseous mixtures which contain such anhydride vapor.

Turning first to maleic anhydride scrubbers, maleic anhydride is conventionally recovered from such gaseous mixtures by first cooling the gas to condense a portion of the maleic anhydride, and then, after separating the condensate, scrubbing the gas stream with a solvent to produce a product which can subsequently be separated from the absorbent and purified. Initially, water was utilized as the solvent for scrubbing the gas stream. A disadvantage to aqueous scrubbing liquids is that the maleic anhydride is converted to maleic acid when contacted with the aqueous liquid. The acid must ultimately be dehydrated to form the desired anhydride. In the process chain, an undesirable by-product may result from the isomerization of a substantial portion of the maleic acid. This by-product is fumaric acid. The conversion of maleic to fumaric acid, even in small amounts, is undesirable because of yield losses, difficulties removing fumaric acid from the process system and difficulties disposing of the fumaric acid.

Because of the difficulties with fumaric acid, other scrubbing agents have been developed including dibutyl phthalate; tricresyl phosphate; dimethyl terephthalate; diphenylpentachloride; dibutyl maleate; high molecular wax; dialkyl phthalate; cycloaliphatic acid ester; dimethylbenzophenone; phthlate ester; and intramolecular carboxylic acid anhydride. Various disadvantages exist with each of these processes. For example, dibutyl phthalate, under commercial temperature conditions, exits the gas scrubbing vessel in the exit gas stream. This cannot be alleviated by lowering the temperature of the scrubbing liquid since the minimum temperature permitted in the gas scrubber is determined by the dew point of water. The scrubbing temperature must be kept above this value in order to prevent the condensation of water. As explained above, if water is present in the system, maleic acid will form by hydrolysis of the anhydride. Maleic acid in turn isomerizes to the undesirable insoluble fumaric acid. This same problem, the production of fumaric acid, is inherent in many of the processes which utilize the above described scrubbing agents because water may be present in the system as a by-product. Therefore, although these processes were intended to alleviate the problem of fumaric acid formation, many still result in the formation of some fumaric acid.

Phthalic anhydride can also be recovered using a number of methods. Multiple switch condensers have been utilized for some time. However, such systems are generally expensive to build and difficult to operate and maintain because of the formation of phthalic anhydride crystals throughout the system. Other methods of phthalic anhydride recovery entirely eliminate the switch condenser and include: water based scrubbers such as those described above; continuous condensation and collection of the phthalic anhydride as a crystal or slurry; scrubbing the gas with a solvent such as dibutyl phthalate; using a moving bed of pebbles; direct contact with a liquid coolant such as $C_nH_{2n+1}$; cooling the gas by vaporization of naphthalene; and compressing the cooled gas to 2-6 atmospheres and re-cooling it to recover the phthalic anhydride as a liquid. Various disadvantages also exist with each of these processes. Because phthalic anhydride crystallizes at a temperature below 268° F., the system in which the above processes is carried out is generally maintained at a temperature of at least 268° F. to prevent the formation of anhydride crystals which could otherwise clog the system (except for switch condensers which cool to less than 268° F. within the condenser). Systems which utilize scrubbing agents at less than 268° F., such as water based scrubbers, are further limited by the continued growth of these insoluble phthalic acid crystals within the scrubber.

Many of the above mentioned maleic and phthalic anhydride scrubbing processes yield a product which must be further refined to purify the scrubbed anhydride, especially if the process involves use of an absorbent. U.S. Pat. No. 3,965,123 teaches a process for recovery of maleic anhydride which comprises absorbing the maleic anhydride into an organic absorbent, distilling the maleic anhydride from the resulting absorbent, condensing the liquid maleic anhydride, and distilling the condensed maleic anhydride from other remaining compounds. U.S. Pat. No. 5,069,687 teaches a process for recovering maleic anhydride from a liquid absorbent wherein the maleic anhydride enriched absorbent is contacted with a water absorbent to reduce the water content of the enriched absorbent. The enriched absorbent is then dried to obtain a solid product which is recovered. Refinement following absorption is disadvantageous because the processes are time consuming and require large amounts of energy.

Furthermore, if the above mentioned stripping processes are intended simply to remove vaporous maleic and phthalic anhydride from gaseous mixtures before the gaseous mixtures are released into the atmosphere, disposal of the anhydride enriched absorbent is costly and subject to rigid environmental regulations.

Therefore, the need exists for an economical and inexpensive apparatus and process which can capture airborne anhydrides. The process should yield a product which can be readily utilized without further refinement. It would also be desirable if no waste were produced from the process. The apparatus should be disposed to receive and collect different types of airborne anhydrides within a single system. Finally, the apparatus should inhibit the formation of anhydride crystals throughout the system to prevent clogging and breakdown.

SUMMARY OF THE INVENTION

These and other advantages are achieved in an apparatus and process for the recovery of airborne anhydrides such as maleic or phthalic anhydride vapors or trimellitic or succinic anhydride dust, wherein these airborne anhydrides are contacted with a hot glycol, such as diethylene glycol, in the liquid phase to first dissolve and then react with the airborne anhydrides yielding a useable product, such as maleic and phthalic half-esters. Preferably the system in which the process is practiced, as well as the diethylene glycol, is maintained at a temperature of at least 270° F. to prevent the formation of phthalic anhydride crystals. The apparatus and process of the present invention is effective in capturing airborne anhydrides such as maleic or phthalic anhydride vapors or trimellitic or succinic anhydride dust, reacting these dissolved anhydrides and yielding a useable half-ester/glycol by-product solution which can be utilized as a raw material for the production of thermoset resins, thermosetting polyester resins, thermosetting acrylic vinyl ester polymers, alkyds, etc.

In the preferred embodiment, phthalic anhydride vapor is introduced at the top of a venturi where the vapor is contacted with hot diethylene glycol. The phthalic anhydride vapor dissolves in the hot glycol and then reacts with the glycol to form phthalic half-esters. The venturi enhances the contact between the glycol and the phthalic anhydride vapor, facilitating the dissolution of phthalic anhydride vapor in the hot glycol.

Maleic anhydride vapor is introduced at the discharge side of the venturi such that the maleic anhydride vapor dissolves in unreacted hot glycol to form maleic half-esters. Since the system is maintained at a temperature at which the reaction rate of maleic anhydride vapor and hot glycol is essentially instantaneous, the additional contact time necessary for the phthalic anhydride/glycol reaction is not required. The phthalic half-esters, the maleic half-esters and the unreacted diethylene glycol then flow into a collection tank from which the liquid mixture is circulated back through the venturi and other parts of the system.

Any maleic or phthalic anhydride vapors remaining after the venturi, i.e., the first stage of contact with hot glycol, are directed through a conventional packed column. In the packed column or second stage, residual anhydride vapors are again contacted with diethylene glycol solution to dissolve and react to form half-esters. Again, the phthalic half-esters, the maleic half-esters and the unreacted diethylene glycol from the second stage then flow back into the collection tank from which the liquid mixture is circulated back through the venturi and packed column.

In one alternative embodiment, the venturi of the first stage is replaced with a packed column.

The above described system is equally effective in dissolving and reacting other types of airborne anhydrides such as trimellitic or succinic anhydride dust.

The primary advantage of such a system and method is that airborne anhydrides can be effectively prevented from venting to the atmosphere with one combined system such that a separate scrubber is not required for each type of anhydride. Further, the products of this process can be utilized for other processes, such that no waste is produced. Additionally, the entire recovery process can be made continuous by integrating the scrubber with anhydride storage tank systems or anhydride handling systems.

Another advantage of the above described invention is that a single system can be used to separately treat different types of airborne anhydrides. For example, in the production of thermoset resins, thermosetting polyester resins, thermosetting acrylic vinyl ester polymers, alkyds, etc., it is common to utilize several types of anhydrides. By separating the vapor line inlets, such as above and below the venturi, anhydride vapors from one anhydride tank are prevented from migrating into the other anhydride tank, thus avoiding vent line plugging, contamination, etc.

BRIEF DESCRIPTION OF THE DRAWINGS

In the drawings which illustrate those which are presently regarded as the best modes for carrying out the invention.

DETAILED DESCRIPTION OF THE PREFERRED EMBODIMENT

The apparatus and process of the present invention collects airborne anhydrides such as vapor and dust from gaseous mixtures by contacting the airborne anhydrides with heated glycol in the liquid phase. Upon contact, the airborne anhydrides dissolve in the glycol and react to form half-ester by-products. Although the point of introduction of the gaseous anhydride mixture into the system may vary depending on the reaction rate of the anhydride with the glycol, the invention permits various types of airborne anhydrides to be collected within a single unit. Additionally, the invention is not limited by the phase of the airborne anhydride; it is equally effective in collecting anhydride dust, generated from solid anhydrides such as trimellitic or succinic anhydride, or anhydride vapor, generated from liquid anhydrides such as maleic or phthalic anhydride.

In the Figures, like numerals are employed to designate like parts through the drawings, and various pieces of equipment, such as valves, fittings, pumps, and the like, are omitted so as to simplify the description of the invention. However, those skilled in the art will realize that such conventional equipment can be employed as desired.

Figure 1:
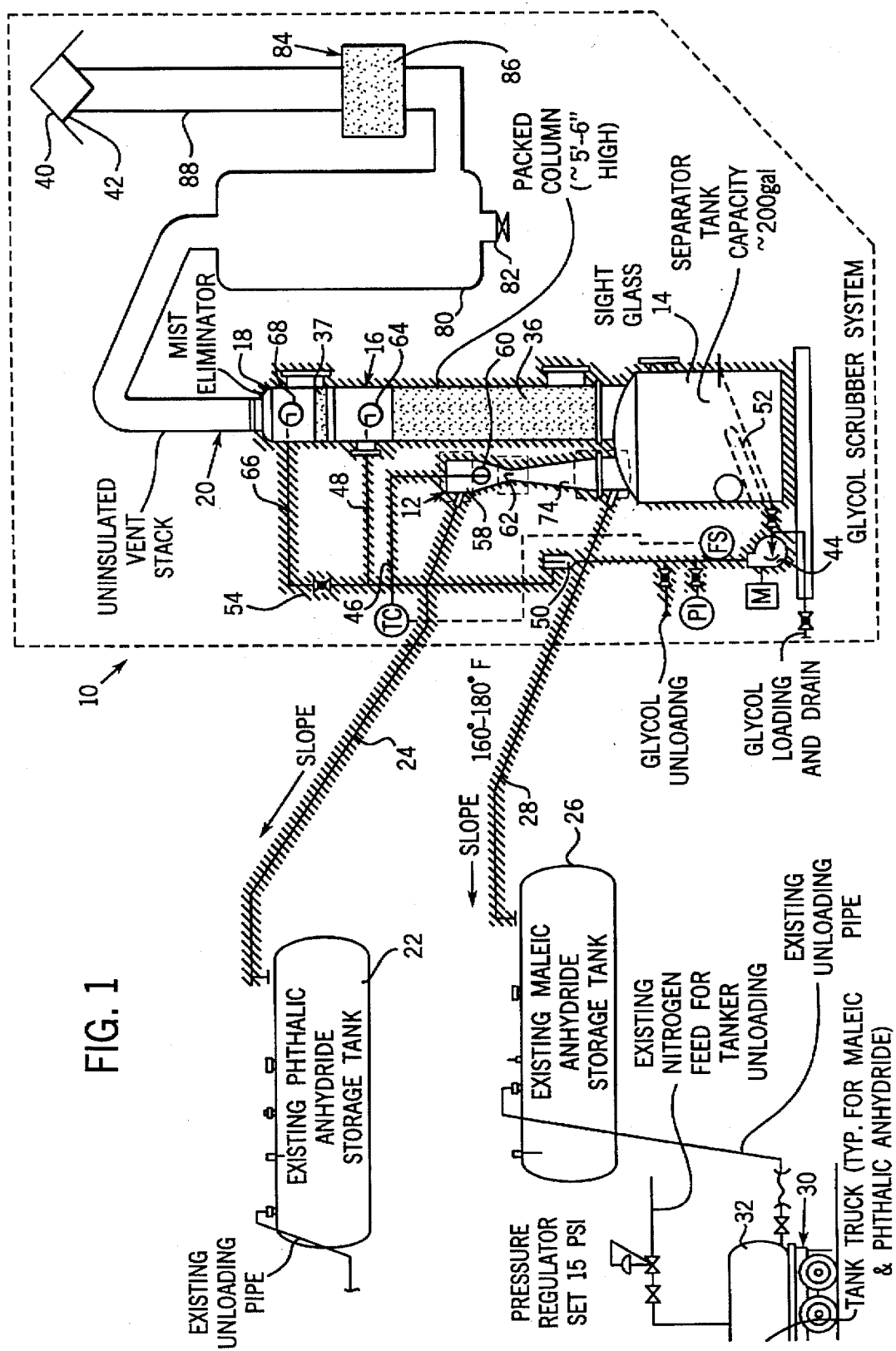
FIG. 1 illustrates the glycol vapor collection apparatus used to carry out the process of the invention.

Referring now to FIG. 1, a preferred embodiment of the glycol scrubber apparatus 10 used to practice the process of the present invention is illustrated. In this embodiment, the apparatus and process are utilized to collect maleic and phthalic anhydride vapors present in the transfer and storage of the corresponding liquid anhydrides. The products of the reactions between the glycol and the maleic and phthalic anhydride vapors are maleic half-esters and phthalic half-esters, respectively. Scrubber apparatus 10 is comprised generally of venturi 12, separator tank 14, packed column 16, mist eliminator 18, and glycol vapor condensation tank 80. Liquid phthalic anhydride is stored in phthalic anhydride storage tank 22 which is in fluid communication with scrubber apparatus 10 by way of phthalic anhydride vapor line 24. Liquid maleic anhydride is stored in maleic anhydride storage tank 26 which is in fluid communication with scrubber apparatus 10 by way of maleic anhydride vapor line 28. Glycol supply line 46 supplies hot glycol to the top of venturi 12, adjacent the inlet for phthalic anhydride vapor line 24. The glycol in apparatus 10 is maintained at a temperature of at least 270° F. so that it can be introduced to the top of venturi 12 in a liquid/molten phase. Because the reaction rates between the individual anhydrides and the hot glycol are different, i.e., particular types of anhydrides may require more reaction time than others at a given temperature, the points of introduction of vapor lines 24, 28 from the individual anhydride storage tanks vary. For example, because the temperature of the system is maintained between 270° F. and 320° F., maleic anhydride vapor dissolves and reacts with the hot glycol almost instantaneously whereas the reaction rate of phthalic anhydride vapor with the hot glycol is slower. Therefore, phthalic anhydride vapor is introduced into apparatus 10 and contacted with hot glycol at a point in the system, i.e., the top of venturi 12, above the introduction point of maleic anhydride vapor, thus permitting a longer reaction time. The apparatus and method of this invention can collect both the small amounts of maleic and phthalic anhydride vapors that accumulate in tanks 22 and 26 during storage, as well as the large amounts of maleic and phthalic anhydride vapors which are present during loading of tanks 22 and 26. Tank truck 30 having a container 32 is depicted as it would appear during the loading of liquid maleic anhydride storage tank 26.

Venturi 12 is in fluid communication with separator tank 14 such that the solution of phthalic half-esters and excess glycol from the top of venturi 12 drains into separator tank 14. Packed column 16 is also in fluid communication with separator tank 14 such that any solution introduced or formed within packed column 16 will also drain into separator tank 14. Packed column 16 can contain any standard packing material 36.

Located above and in fluid communication with packed column 16 is mist eliminator 18 which also contains packing material 36. Stack 20 is attached above mist eliminator 18 to receive glycol effluent which may have been introduced in mist eliminator 18. Glycol effluent passing through stack 20 migrates into glycol condensation tank 80. Attached to condensation tank 80 is glycol demister 84 which contains packing material 86. Attached atop demister 84 is uninsulated stack 88 which vents to the atmosphere. Roof 40 is attached to the open end of stack 88 to inhibit foreign material from entering glycol scrubber system 10. Accumulation dish 42 is attached between stack 88 and roof 40 and also serves to inhibit foreign material from entering glycol scrubber apparatus 10.

Recirculation pump 44 is in fluid communication with separator tank 14 to supply hot glycol to venturi 12 and packed column 16 through glycol supply lines 46 and 48, respectively.

In-line heater 50 is located between recirculation pump 44 and glycol supply lines 46 and 48 to heat the glycol before it is discharged into venturi 12 and packed column 16. Additionally, heating coil 52 is located within separator tank 14 to pre-heat the glycol before it is circulated by recirculation pump 44.

Except for stack 20, glycol condensation tank 80, glycol demister 84, stack 88, roof 40 and dish 42, glycol scrubber apparatus 10 is encased in insulation 54.

Finally, the system is charged with diethylene glycol to circulate through venturi 12 and packed column 16.

Turning now to the operation of glycol scrubber apparatus 10, phthalic anhydride vapors are introduced through phthalic anhydride vapor line 24 at the top of venturi 12. Venturi nozzle 60, also located at the top of venturi 12, introduces hot diethylene glycol such that the phthalic anhydride vapors introduced by line 24 are contacted with a spray of liquid diethylene glycol. Upon contact, phthalic anhydride vapors dissolve in the diethylene glycol and then react to form phthalic half-esters. Venturi nozzle 60 is utilized to create a fine spray of liquid diethylene glycol so that surface area contact with the phthalic anhydride vapors is enhanced. The primary function of venturi 12 is to further enhance the mixing of, and thus the reaction between, phthalic anhydride vapors and the diethylene glycol. Specifically, the increased velocity of the unreacted elements as they pass through venturi throat 62 facilitates mixing.

Maleic anhydride vapors are introduced through maleic anhydride vapor line 28 at the discharge of venturi 12. At this point, unreacted diethylene glycol draining through venturi 12 is contacted with maleic anhydride vapors, such that the maleic anhydride vapors dissolve in the glycol and react to form maleic half-esters.

The maleic and phthalic half-esters, along with any unreacted diethylene glycol, collect in separator tank 14. Any remaining maleic and phthalic anhydride vapors which have not been collected migrate into packed column 16 where the vapors are again contacted with a fine spray of hot liquid glycol. As the vapors migrate through packed column 16, packing material 36 serves two purposes. First, packing material 36 acts as a matrix on which remaining maleic and phthalic anhydride vapors can condense. Second, packing material 36 disperses the flow of the vapors throughout the interior of packed column 16 so that the vapors are more readily contacted with diethylene glycol introduced through packed column nozzle 64, located at the top of packed column 16. Again, as the diethylene glycol is contacted with vaporous maleic and phthalic anhydride, the vapors dissolve in the glycol and react to form maleic and phthalic half-esters. These half-esters, along with any unreacted liquid diethylene glycol, flow back down through packed column 16 and collect in separator tank 14.

Mist eliminator 18 functions to remove diethylene glycol vapors which may have inadvertently been introduced into the system along with the liquid diethylene glycol. The diethylene glycol vapors contact packing material 37 and condense on the surface of the packing material.

Stack 20, glycol condensation tank 80, glycol demister 84 and stack 88 are also utilized to condense glycol vapors which may still be present in the system following mist eliminator 18. Specifically, because stacks 20 and 88 are uninsulated, they remain substantially at atmospheric temperature so that glycol vapors which come into contact with the walls of stacks 20 and 88 will condense and flow back down into the system. Glycol condensation tank 80 serves substantially the same purpose, although a larger wall area is provided on which vaporous glycol can condense. Additionally, tank 80 serves as a collection tank for condensed glycol. The condensed glycol collected in tank 80 can be removed from the tank by way of valve 82 which can be connected by piping (not shown) to direct the glycol back into separator tank 14.

Glycol demister 84 is a further means for collecting glycol vapor before it vents to the atmosphere. Again, demister 84 is uninsulated to facilitate condensation. Packing material 86 provides additional surface area on which the vaporous glycol can condense. Finally, dish 42 can also serve as a collector plate on which remaining glycol vapors can condense.

The temperature of the system is significant for several reasons. First, because phthalic anhydride vapors sublime at temperatures below 268° F., it is necessary to generally maintain the system at temperatures above 268° F. to ensure that phthalic anhydride crystals do not form. As mentioned above, the formation of phthalic anhydride crystals can plug the circulation system and decrease the efficiency of glycol scrubber apparatus 10.

Second, although it is necessary to keep the system at temperatures above the sublimation temperature of phthalic anhydride vapors, it is also necessary to generally maintain the system at a temperature below 380° F. to prevent the formation of undesirable by-products. If the temperature of the half-esters formed in the system is allowed above 380° F., the half-esters will continue to react to form diesters and water. Once water has been introduced in the system, phthalic and maleic acid can form, which in turn leads to the formation of fumaric acid. Therefore, the system is generally maintained at a temperature well below 380° F.

Finally, because the invention generally utilizes diethylene glycol in the liquid/molten phase, a glycol temperature range between 270° F. and 320° F. is generally maintained.

To maintain the proper temperature of the system, in-line heater 50, heater coils 52 and insulation 54 are utilized. As recirculation pump 44 moves the glycol solution of separator tank 14 to venturi nozzle 60 and column nozzle 64, in-line heater 50 contacts the solution and raises the temperature of the solution to a range between 270° F. and 320° F. It has been found that heating the solution in this manner, as opposed to heating the solution in separator tank 14, is more effective and energy efficient. However, heater coils 52 are used to maintain a predetermined solution temperature in separator tank 14 so that the solution is pre-heated before it is contacted with in-line heater 50. Lastly, because of the need to ensure that vaporous phthalic anhydride remains at a temperature above 268° F. as it passes through the system, those portions of the system through which phthalic anhydride vapor may pass are encased with insulation 54 to ensure that there are no "cold spots" in the system where such crystals might form.

As mentioned previously, it is desirable to separate the points at which phthalic and maleic anhydride vapors are introduced into glycol scrubber apparatus 10. These anhydride vapors are introduced into the system at separate points for a number of reasons. First, it is desirable to maintain separation between the two points of introduction so that vapors from one liquid anhydride storage tank will not migrate into the other tank. Venturi 12 is useful in this regard. The pressure drop in venturi throat 62 prevents maleic anhydride vapor from migrating back through venturi 12 and into phthalic vapor line 24. Conversely, because substantially all of the phthalic anhydride vapor reacts with the hot diethylene glycol in the top and throat of venturi 12, there is little possibility that any remaining phthalic anhydride vapor will migrate up maleic anhydride vapor line 28.

The second reason that maleic and phthalic anhydride vapors are introduced at two different points in the system is because of the difference in reaction times between phthalic and maleic anhydride vapors when dissolved in glycol. Vaporous phthalic anhydride reacts at a temperature of approximately 240° F. However, vaporous maleic anhydride reacts at a temperature of approximately 170° F. Therefore, if the system is maintained at a temperature of between 270° F. and 320° F., the reaction rate between vaporous maleic anhydride and glycol will be much faster, i.e., almost instantaneous, compared to the reaction rate between vaporous phthalic anhydride and glycol. It has been found that the best results are achieved by introducing vaporous phthalic anhydride into the system before vaporous maleic anhydride so that the phthalic anhydride vapor has more time to react with the diethylene glycol.

There is also a need to prevent half-esters and diethylene glycol in either vapor or liquid form from migrating into phthalic anhydride tank 22 or maleic anhydride tank 26, where the glycol could react to form half-esters. Therefore, phthalic anhydride vapor line 24 and maleic anhydride vapor line 28 are preferably angled so that any half-esters that may form in the lines will flow by gravity back into glycol scrubber apparatus 10 and drain down into separator tank 14.

Turning next to the method by which the maleic and phthalic anhydride vapors are driven through the system, although a typical scrubber containing a venturi may utilize the pressure drop created in the venturi to drive gas through the scrubber, venturi 12 of the present invention is not the impetus of the vapor movement through glycol scrubber apparatus 10. Instead, glycol scrubber apparatus 10 utilizes pressure in tanks 22 and 26 to serve as the mechanism by which vapor is driven through the system. Because glycol scrubber apparatus 10 is open to the atmosphere, the pressure created in tanks 22 and 26 during storage and unloading are sufficient to drive vaporous anhydride through the system.

The greatest loads on the system are created when liquid maleic and phthalic anhydrides are transferred into their respective storage tanks. During a typical loading procedure, container 32 of tank truck 30 is in fluid communication with a liquid anhydride storage tank. Container 32 is maintained at a higher pressure than the anhydride storage tank so that liquid anhydride within container 32 will flow into the storage tank. The pressure in container 32 is typically maintained through the use of a non-reactive gas. By way of example, but not intended as a limitation, nitrogen gas maintained at a pressure of 15 psi can be used to generate this pressure.

During loading, two vaporous gas surges generally occur. The first surge is created by the displacement of the large volume of vapor within the storage tank as liquid anhydride flows into the storage tank. A gaseous mixture containing anhydride vapor is forced through the tank's anhydride vapor line and into glycol scrubber apparatus 10. The flow rate of the first surge has been found to be approximately 20 CFM. The second surge occurs as container 32 is emptied. When all of the liquid anhydride has flowed from container 32, the gas used to drive the liquid anhydride into the anhydride storage tank is also allowed to flow into the tank. This is to prevent anhydride vapors already circulating through glycol scrubber apparatus 10 from being drawn back into the storage tank being filled. The gas used to drive the liquid anhydride into the storage tank subsequently migrates into glycol scrubber apparatus 10, through which it passes unreacted, and is released into the atmosphere. The flow rate of the second surge may be as high as 900 CFM.

Although any member of the glycol family may be used in the practice of the above described process, it has been found that diethylene glycol is especially effective in the practice of this invention. The process has been found to be most effective when the circulated solution of half-esters and glycol is drained from the system before all the glycol is reacted; the system is then re-charged with additional glycol. Preferably, the percentage of free glycol in the system is always large enough that the reaction rate between dissolved anhydride and glycol is maximized.

Although the invention has been described using maleic and phthalic anhydride vapor, it should be understood that the invention is equally effective in collecting other types of airborne anhydrides and is not limited to use with only maleic and phthalic anhydrides. For example, if the scrubber were to be used in connection with liquid phthalic anhydride and solid trimellitic anhydride, a scrubber for collecting phthalic anhydride vapor and trimellitic anhydride dust may be constructed.

In one alternative embodiment illustrated in FIG. 1, an additional glycol supply line 66 can be used to introduce hot glycol into mist eliminator 18 by way of mist eliminator nozzle 68. This alternative embodiment can be used to scrub remaining anhydride vapors which may have passed unreacted through packed column 16.

Figure 2:
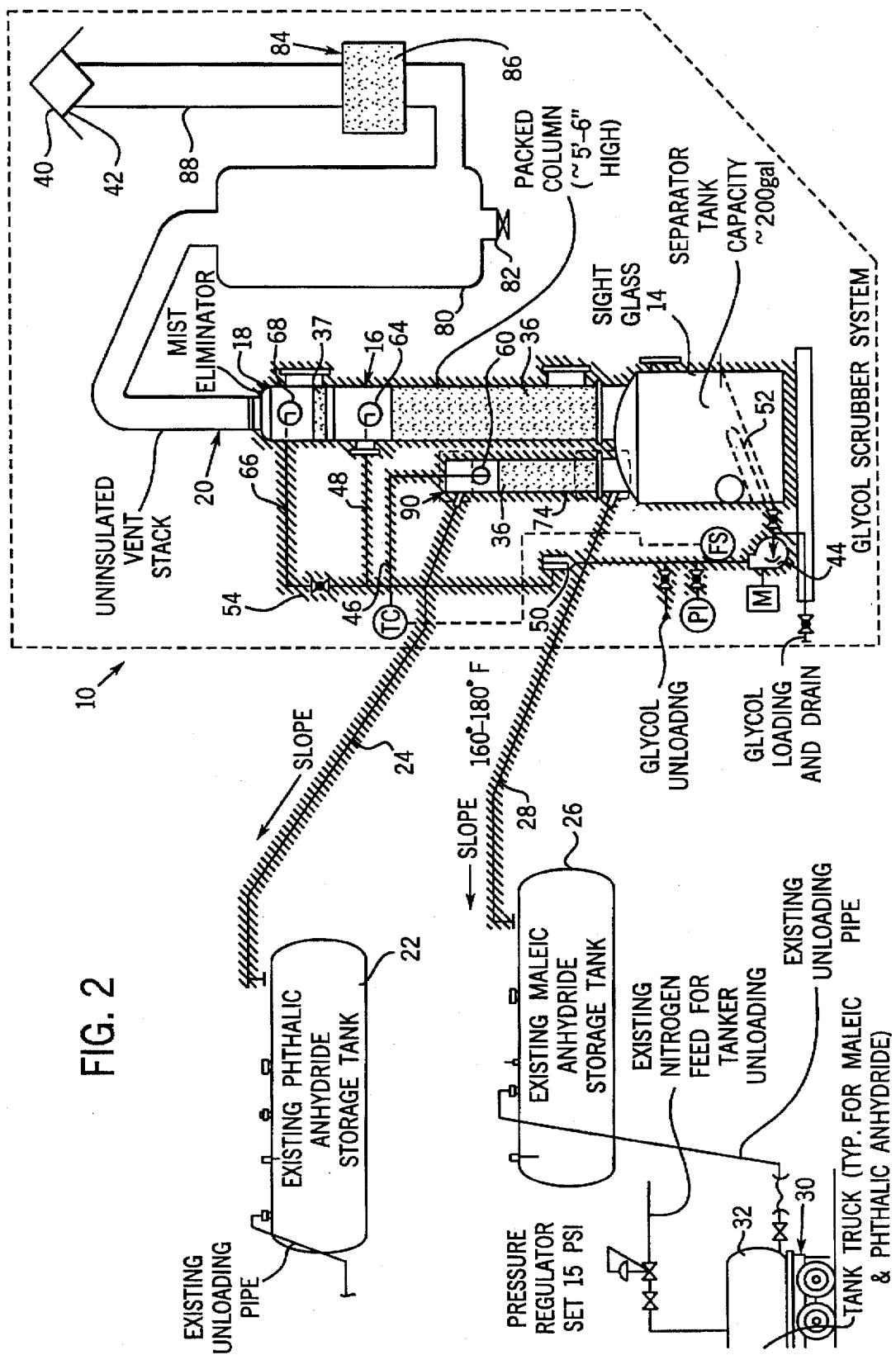
FIG. 2 illustrates another embodiment of the apparatus of the present invention in which a packed column replaces the venturi of the apparatus illustrated in FIG. 1.

Those skilled in the art will understand that additional configurations of the system are possible without departing from the spirit of the invention, i.e., the use of heated glycol as a means for collecting airborne anhydrides. In FIG. 2, another alternative embodiment of the invention is shown. Specifically, venturi 12 can be removed altogether and replaced with another packed column 90.

In yet other embodiments, a series of packed columns may be utilized or venturi 12 can be removed altogether and the single packed column 16 can be heightened to increase the effectiveness of the column. The specific configuration for a particular glycol scrubber will vary depending on the number of different anhydrides with which the system is used and the individual chemical and physical characteristics of those anhydrides.

Additionally, although the invention of the present system is intended to be used primarily as a means for controlling airborne anhydrides which may be present during storage and transfer of anhydrides, hot glycol can also be utilized as an absorbent in scrubber systems such as those described in the prior art.

Although the invention has been described in considerable detail through the figures and above discussion, many variations and modifications can be made by one skilled in the art without departing from the spirit and scope of the invention as described in the following claims.

What is claimed is:

1. A process for the collection of phthalic and maleic anhydride vapors wherein said process is carried out in an apparatus having a first zone in fluid communication with a second zone, the process comprising the steps of
   a. introducing phthalic anhydride vapor into the first zone;
   b. contacting phthalic anhydride vapor in the first zone with heated glycol to form a solution of phthalic half-esters and glycol;
   c. introducing maleic anhydride vapor into the second zone;
   d. contacting the maleic anhydride vapor with the heated glycol solution from the first zone to form a solution of phthalic half-esters, maleic half-esters and glycol.

2. The process of claim 1 wherein the process further comprises the step of heating said glycol to a temperature of at least 268° F. before it is contacted with phthalic anhydride vapor.

3. The process of claim 1 wherein the glycol is diethylene glycol.

4. The process of claim 1 wherein the first zone comprises a packed column.

5. The process of claim 1 wherein the first zone comprises a venturi column.

6. The process of claim 1 wherein the second zone comprises a packed column.

7. The process of claim 1 wherein the second zone comprises a venturi column.

8. A process for the recovery of phthalic and maleic anhydride vapors wherein said process is carried out in an apparatus having a first zone, a second zone, and a third zone all in fluid communication with one another, the process comprising the steps of
   a. introducing phthalic anhydride vapor into the first zone;
   b. contacting phthalic anhydride vapor in the first zone with the heated glycol to form a solution of phthalic half-esters and glycol;
   c. introducing maleic anhydride vapor into the second zone; and
   d. contacting the maleic anhydride vapor with the glycol solution from the first zone to form a solution of phthalic half-esters, maleic half-esters and glycol.

9. The process of claim 8, further comprising the steps of
   a. passing any remaining phthalic anhydride vapor or maleic anhydride vapor into the third zone;
   b. contacting the remaining phthalic anhydride vapor or maleic anhydride vapor with heated glycol.

10. The process of claim 8 wherein the process further comprises the step of heating said glycol to a temperature of at least 268° F. before it is contacted with phthalic anhydride vapor.

11. The process of claim 8 wherein the glycol is diethylene glycol.

12. The process of claim 8 wherein the first zone comprises a packed column.

13. The process of claim 8 wherein the first zone comprises a venturi column.

14. The process of claim 8 wherein the second zone comprises a packed column.

15. The process of claim 8 wherein the second zone comprises a venturi column.

16. The process of claim 8 wherein the third zone comprises a packed column.

17. The process of claim 8 wherein the third zone comprises a venturi column.

18. A process for the recovery of airborne anhydrides comprising the steps of
   a. heating glycol to a temperature of at least 268° F.;
   b. contacting airborne anhydride with the heated glycol to form a solution of glycol and half-esters.

19. The process of claim 18 wherein the glycol is diethylene glycol.

* * * * *